United States Patent [19]
Griffin

[11] Patent Number: 5,241,803
[45] Date of Patent: Sep. 7, 1993

[54] OZONE STERILIZATION METHOD AND PRODUCT

[76] Inventor: David Griffin, P.O. Box 200, Irvington, N.Y. 10533

[21] Appl. No.: 849,195

[22] Filed: Mar. 11, 1992

[51] Int. Cl.$^5$ .............................................. B65B 55/10
[52] U.S. Cl. .................. 53/425; 53/111 RC; 53/426
[58] Field of Search ................. 53/425, 426, 431, 428, 53/111 RC, 111 R

[56] References Cited

U.S. PATENT DOCUMENTS

| | | | |
|---|---|---|---|
| 2,917,878 | 12/1959 | Carnarius et al. | 53/426 |
| 3,726,057 | 4/1973 | Kemble | 53/425 |
| 3,815,315 | 6/1974 | Glick | 53/425 |
| 4,470,240 | 9/1984 | Torterotot et al. | 53/425 X |
| 4,603,538 | 8/1986 | Shave | 53/425 |
| 5,014,494 | 5/1991 | George | 53/425 |

Primary Examiner—James F. Coan
Attorney, Agent, or Firm—Handal & Morofsky

[57] ABSTRACT

A method of sterilizing medical products with an ozone-rich atmosphere is disclosed. The method avoids contamination problems that can arise under prior art ethylene oxide sterilization methods. Moderate, carefully controlled conditions are used. The method is particularly suited to the sterilization of sensitive materials such as catgut, polyglycolics and other absorbable synthetic polymeric replacements for catgut. The invention includes sterilized products produced by these methods.

11 Claims, No Drawings

OZONE STERILIZATION METHOD AND PRODUCT

TECHNICAL FIELD

The present invention relates to the sterilization of small articles, for example, surgical devices and supplies. Such articles include surgical staples and sutures.

BACKGROUND

The need for thorough sterilization of surgical implements and supplies is of course well known and painstaking and expensive steps are often taken to ensure the highest levels of sterility for medical supplies and equipment.

By way of example of a well developed field of prior art is a series of patents to Glick, including U.S. Pat. Nos. 3,728,839, 3,815,315 and 4,135,622 which relate to the particular problems encountered in sterilizing absorbable sutures without degrading them, and especially in sterilizing sutures and other medical devices made of polyglycolic acid.

U.S. Pat. No. 3,549,528 to Armstrong discloses a liquid-phase process for sterilization of surgical or medical instruments using ozonized oxygen. The liquid phase (typically aqueous) is pretreated under pressure with turbulence, to achieve maximum uniformity of oxygen-ozone concentration throughout the fluid. Such a liquid phase sterilization process is not appropriate for small medical devices, including absorbable sutures, staples and the like, which can be sensitive to moisture, and are subject to decomposition or degradation.

As reported by Armstrong, ozone is contraindicated as a gas-phase sterilant for medical equipment and supplies because of the difficulty in controlling the concentration and the consistent effectiveness of ozone. (Col. 1 lines 67-69.)

SUMMARY OF THE INVENTION

This invention solves a problem. In particular it solves the problem of providing an improved method of sterilization which is reliable, safe, and non-destructive for metallic surgical elements, and even for sensitive, polymeric and biological materials, while at the same time being non-contaminating and non-polluting. Still more particularly, the invention provides such a method which is suitable for sterilization of supplies or devices in packages that are sealed after sterilization.

While Glick discloses such a package in the form of a multi-layer envelope including a laminated sheath in which aluminum foil is sandwiched between polyethylene layers and the envelope is further sealed within a paper pouch, Glick uses ethylene-oxide sterilization.

I have discovered that although widely practiced, ethylene oxide sterilization methods can suffer from the drawback of residual contamination of the package or the sterilized contents by the ethylene oxide, or by gaseous contaminants associated with ethylene oxide gas technology or by reaction products of these gases with the package material or contents. Another possible route of contamination or retention of ethylene oxide in the package for subsequent release is by absorption by or coating of the polymeric liner, for example polyethylene, which is usually used to provide a heat-sealable envelope.

Ethylene oxide is an extremely noxious explosive material, gaseous at warmer room temperatures, but liquid at cooler room temperatures (below 12° C., 53° F.). It is probably carcinogenic, and is highly irritating to eyes and mucous membranes It has also been linked to pulmonary edema. Substantial residues from ethylene oxide treatment can clearly pose a hazard to workers exposed to them, and may constitute an environmental hazard from significant quantities of contaminated packaging. Because of its unpleasant characteristics, ethylene oxide treatments are complex and expensive, employing, for example, polyhalogenated alkane gases such as Freon (DuPont), as diluents to nugate its explosivity. Such gases are expensive and require careful confinement to avoid deleterious environmental consequences.

Accordingly, the present invention provides a method of sterilizing supplies and devices of a size that can readily be handled manually, especially medical supplies and devices, which method comprises treating such supplies and devices in an enclosed environment with an ozone atmosphere in which ozone is present at a sufficient concentration to be an effective sterilant. The method is preferably conducted under moderate conditions of temperature, pressure and time to provide effective sterilization without degrading sensitive medical materials such as catgut or polyglycol. Clearly, stainless steel surgical elements, such as surgical staples, can withstand more rigorous conditions.

DETAILED DESCRIPTION OF THE PREFERRED EMBODIMENTS

The duration of the ozone treatment should be quite short for non-metallic products. Because of the efficacy of ozone, whereas an hour may produce particularly thorough sterilization of stainless steel products, less than ten minutes and preferably from 1 to 5 minutes is adequate for destructible materials such as polyglycol and catgut. Excessive ozone exposure can degrade sensitive materials.

Moderate temperatures not exceeding 100° F. are desirable, while room-temperature treatments of from 60° to 80° F. are preferred.

Pressures below one atmosphere gauge are effective, with from five to ten psig being preferred.

The particular reaction conditions chosen will depend upon the concentration of ozone.

Since high concentrations of ozone are expensive and could be unduly reactive, diluted ozone is preferred. The ozone concentration is preferably less than 25 percent, and more preferably 10 percent or under with from about 2 to about 6 percent, by volume, being practical, the balance being an inactive diluent which can include oxygen.

Polyhalogenated alkanes, such as Fluon, used by the prior art as diluents for ethylene oxide, are not needed for ozone. Suitable diluents include air and other oxygen-containing gaseous mixtures, though care must be taken to avoid oxidation of the package liner or contents Preferred diluent gases include inactive or inert gases or gaseous mixtures such as nitrogen, or deoxygenated air, carbon dioxide and argon.

An ozone-rich atmosphere for use in the process of the invention can be provided in situ by electrical discharge treatment of air, to provide a concentration of from 1 to 10% ozone, preferably from 2 to 6 percent. It is desirable to control and monitor the ozone concentration so that its limits of variation are known and stabilized for effective management of the sterilization process.

Furthermore, accurate control of the sterilization conditions with verification of efficacy permits its optimization to avoid degradation of the sterilized product while obtaining acceptable levels of or acceptable confidence levels of sterilization.

These considerations are of course important for the sensitive materials mentioned above, notably catgut and polyglycolic acids. Such materials are well known to the art, as are their embodiments in orthopedic and surgical devices and in sutures, staples, dressings, swabs and bandages, as is disclosed in some detail in the Glick patents cited above, the disclosures of which are herein incorporated by reference thereto Because of the sensitivity of polyglycolic acids to moisture, the treatment process of this invention is effected under dry conditions when employed for sterilizing such materials. The use of an ozone atmosphere in the manner of this invention is particularly well suited to such a dry process.

The invention can be carried out using a package for the sterilized contents which is substantially as disclosed in the Glick patents. Such a package comprises an envelope of multilayer material which material is a sandwich of aluminum foil between heat-sealable polymeric inner and outer liners. The polymer, as mentioned above, can be polyethylene and is sealed into an open pouch. The pouch is filled with items or materials which are sterilized in a first sterilization step in the open pouch by maintaining the contents and the pouch in an ozone-rich atmosphere of particular concentration for a period of time sufficient to kill any undesirable organisms on the pouch and its contents. The pouch is then heat-sealed across its opening, while still in a sterile atmosphere. The foil filling to the laminate package wall provides a moisture barrier. This inner sealed, sterilized package is further sealed inside a strippable paper outer package or wrapper, which may contain printed information about the contents and which may be subjected to a second sterilization step.

The present invention extends to a packaging and sterilization method which is of the type disclosed in the Glick patents, with the difference that an ozone-rich atmosphere, as described above, is used in place of the ethylene-dioxide-containing gas or gaseous mixture disclosed by Glick and reaction conditions as described herein are used for the ozone treatment.

Thus, the second sterilization step can also be carried out in an ozone-permeable sealed outer package which is not permeable to bacteria, viral, fungal or other bioactive contaminants, or alternatively is sterilized and supplied with a sterile ozone mixture. When the outer package is placed in an atmosphere of ozone, ozone permeates the same, sterilizing the outer package and the inner bag inside it. The sterilization may be carried out by placing the sealed outer package with the sealed inner package inside it in a container in a chamber, having an ozone-rich atmosphere, then transferring the package to a second chamber where the ozone would be removed.

If desired, the loaded package can be evacuated before or after sterilization, or both. Also, the sterilized package can be flushed out with a sterile inert gas, for example nitrogen or air, after sterilization, and such a gas may be sealed in the package.

For moisture-sensitive materials or products, one or more desiccation steps can be included.

To arrest any undesired oxidative effects of ozone, the package can be treated with a reducing agent, for example a hydrogen-containing gas, preferably in a dry gaseous stream to remove any reaction product water vapor, after sterilization. A suitable gas is a dry sterilized stream of nitrogen containing a small proportion of hydrogen by volume, for example 10 percent or less, preferably from 2 to 5 percent.

Alternatively a small quantity of a dry, preferably hygroscopic sterile reducing agent can be included in the package, for example, as a thin layer of slowly oxidizable material in a multilayer package material. Oxidation of the material should not occur so quickly as to outpace sterilization. Any such included reducing agent should however, preferably be biologically innoccuous and absorbable, or well secured to the package, in view of the risk of displacement into a surgical opening in a patient.

EXAMPLE

Three thirty-six inch lengths of polyglycolic acid braided sutures each having a half-circle taper point needle and being wrapped or mounted on separate paper spools, are packaged in a laminar polyethylene-foil envelope, as described above, and sterilized by a method including the following steps. After forming a four-sided envelope and charging it with the sutures, the loaded envelope is placed in a gas permeable container which is not permeable to bacteria and other biological agents, and this container is placed in an ozone sterilizing chamber. The oven is first evacuated and then is charged with a 3% by volume ozone-enriched air at about 70° F. and approximately 10 psig for three minutes with suitable gas-flow agitation to freshen the ozone-rich atmosphere contacting the sutures. The package is flushed with sterilized nitrogen containing a small proportion of hydrogen, such as five percent, and the package is evacuated and sealed in the manner described above.

The product of the method of the example is a sterilized package of sutures free of any ethylene oxide residue or contamination which presents no hazards in handling or disposal.

The invention of course extends to the treatment of a plurality of loaded packages in a batch or continuous process manner. The invention further extends to sterilized products produced by the inventive sterilization methods disclosed herein.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A method of sterilizing a product for use in medical treatment, said product being a sensitive medical material subject to degradation, said method comprising:
   a) charging said product into an open sealable package;
   b) treating said package and product in an enclosed container with an ozone atmosphere in which ozone is present at a sufficient concentration to be an effective sterilant, said treatment having a duration of less than twenty-four hours at a temperature not exceeding 100° F. and at a pressure below one atmosphere gauge and being conducted to provide effective sterilization without degrading said sensitive medical material; and c) sealing said package around said product in a sterile environment to provide a sterilized product.

2. A method according to claim 1 for sterilizing small destructible medical supplies of polyglycol or catgut, wherein said ozone treatment is effected substantially at room temperature for from 1 to 10 minutes at a pressure of from 5 to 10 psig employing a sterilizing atmosphere of dilute ozone at a concentration of from about 2 to about 6 percent by volume.

3. A method as in claim 1, applied to the sterilization of a product selected from the group consisting of stainless steel surgical staples, absorbable sutures, small medical devices and sensitive polymeric and biological materials.

4. A method according to claim 1 wherein said ozone treatment is conducted in a dry atmosphere.

5. A method according to claim 1 wherein said ozone atmosphere comprises ozone in a concentration of from 5 to 25 percent by volume, the balance being an inactive diluent.

6. A method according to claim 1 wherein said product is formed of a material selected from the group consisting of polyglycolic acid and catgut.

7. A method according to claim 1 including flushing the sterilized package with a hydrogen-containing gaseous reducing agent.

8. A method according to claim 1 comprising the step of sealing a reducing agent in said package.

9. A method according to claim 1 including diluting a source of concentrated or nearly pure ozone with a metered proportion of an inactive diluent gas.

10. A method as in claim 1, further comprising the steps of putting said package in an ozone permeable outer envelope, sealing said outer envelope and exposing said sealed outer envelope to an atmosphere containing a concentration of ozone.

11. A sterilized product produced by the method of claim 1.

* * * * *